US006428368B1

(12) United States Patent
Hawkins et al.

(10) Patent No.: US 6,428,368 B1
(45) Date of Patent: *Aug. 6, 2002

(54) SIDE ACTUATED LEAD CONNECTOR ASSEMBLY FOR IMPLANTABLE TISSUE STIMULATION DEVICE

(75) Inventors: Rodney J. Hawkins, Marina Del Rey; Wisit Lim, Palmdale; Buehl E. Truex, Glendora, all of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/817,945

(22) Filed: Mar. 26, 2001

(51) Int. Cl.[7] ............................................... H01R 17/18
(52) U.S. Cl. ........................................ 439/909; 607/37
(58) Field of Search ................................. 439/909, 587, 439/271, 592, 836; 607/37

(56) References Cited

U.S. PATENT DOCUMENTS

| 5,951,595 | A | 9/1999 | Moberg et al. ................ 607/37 |
| 6,192,277 | B1 * | 2/2001 | Lim et al. ...................... 607/37 |

* cited by examiner

Primary Examiner—Gary Paumen
Assistant Examiner—Ann McCamey

(57) ABSTRACT

A setscrewless connector assembly mounted on an implantable tissue stimulation device has an actuator mechanism for fixing, sealing and electrically isolating one or more electrical leads inserted into one or more corresponding lead receptacles within the connector assembly. Fixing and sealing of a lead are accomplished by compressing a resilient lead lock seal of O-ring shape, disposed in an annular recess, with a lip portion of a plunger drawn toward a molded support by the actuator mechanism. In a preferred embodiment, constant-force, high resolution compression of the lead lock seal by the plunger is provided by an actuator comprising a longitudinally extending shaft having a threaded end threadedly coupled to the plunger and an opposite end disposed within the molded support. A driver element, accessible from a side of the connector assembly, is coupled to the opposite end of the threaded shaft. The actuator preferably includes a transmission in which the driver element is journaled in a side wall of the molded support and includes a driver bevel gear in mesh with a driven bevel gear mounted on the opposite end of the threaded shaft. The mechanism is actuated by rotating the driver element by means of a torque limiting wrench. Actuation of the lead fixing and sealing mechanism from the side of the assembly allows insertion and removal of an electrical lead without obstruction.

21 Claims, 10 Drawing Sheets

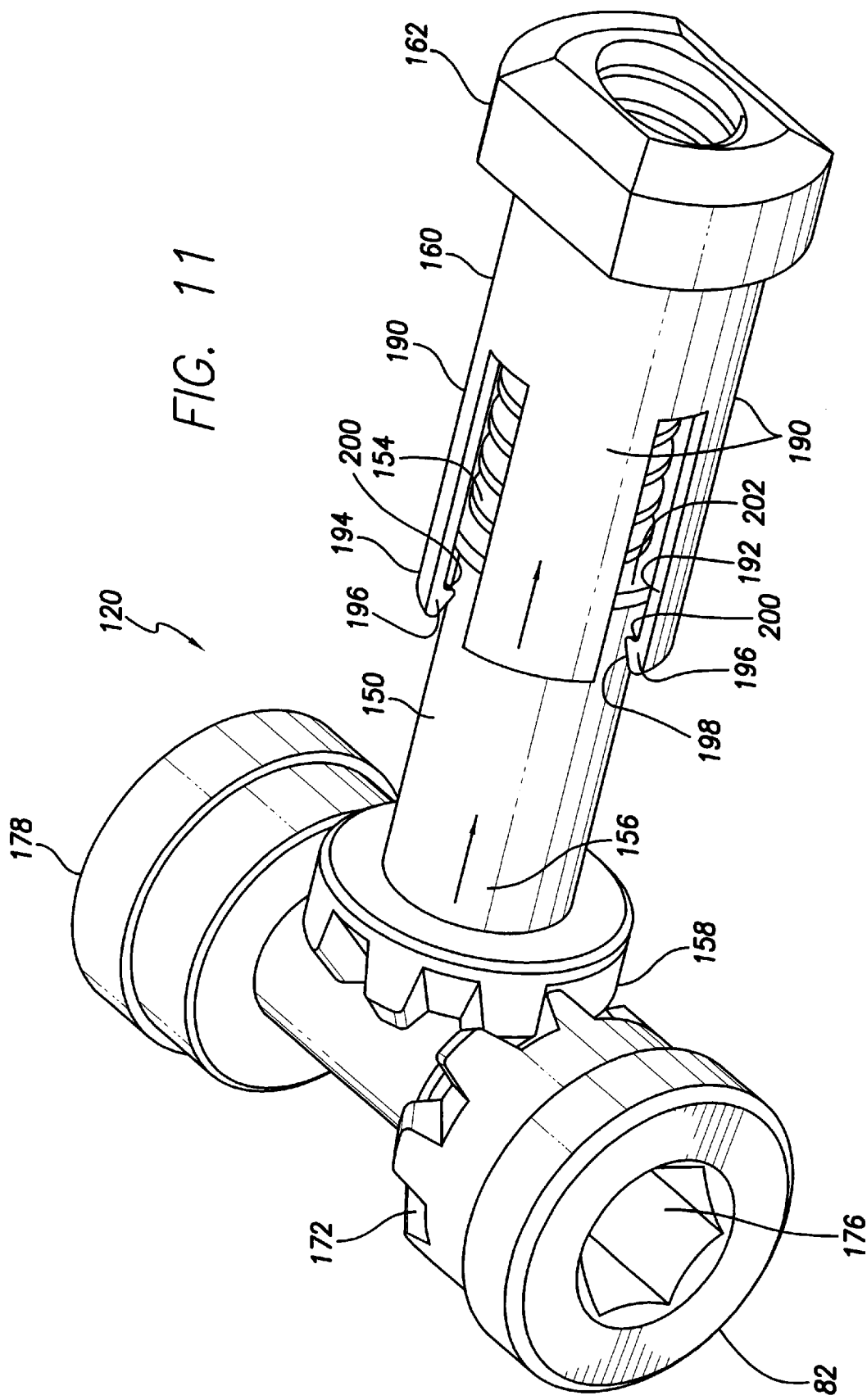

SIDE ACTUATED LEAD CONNECTOR ASSEMBLY FOR IMPLANTABLE TISSUE STIMULATION DEVICE

FIELD OF THE INVENTION

The present invention relates generally to connector assemblies for receiving implantable leads and connecting such leads to electronic circuits within an implantable stimulation device, such as a cardiac pacemaker, and more particularly to a side actuated connector assembly having at least one lead receptacle within which an implantable lead is fixed and sealed.

BACKGROUND OF THE INVENTION

Although it will become evident to those skilled in the art that the present invention is applicable to a variety of implantable tissue stimulation devices utilizing pulse generators to stimulate selected body tissue, the invention and its background will be described principally in the context of a specific example of such devices, namely, cardiac pacemakers for providing precisely controlled stimulation pulses to the heart and for receiving sensed cardiac signals via an external connector assembly having one or more lead-receiving receptacles. The appended claims are not intended to be limited, however, to any specific example or embodiment described herein.

Cardiac pacemakers, and other implantable stimulation devices such as cardiac defibrillators, are hermetically packaged to isolate the device from the body environment. Such devices require that electrical signals be reliably passed between the packaged device and its external connectors, without compromising the hermeticity of the package. Depending on the configuration of the implantable device, there may be multiple electrical paths required between the device and its external connectors for delivering, for example, multi-chamber or multi-site stimulation and shock therapy, and receiving sensed cardiac signals. These paths must be electrically and mechanically integrated with the device to provide a safe, long-term connector assembly which does not compromise the hermetic package.

Typically, a hermetic housing feedthrough electrically couples the electronic circuits contained within the device housing to a connector assembly. The feedthrough assembly extends through the hermetically sealed outer wall of the housing and into the connector assembly so as to couple the electronic circuits within the housing to lead-receiving receptacles within the connector assembly. Each lead has one or more terminals, typically in the form of a pin and one or more conductive rings. The pin is electrically coupled to a distal tip electrode and is therefore sometimes called the "tip terminal." When inserted into the lead receptacle of a connector assembly, contacts within the receptacle come into contact with corresponding terminals on the lead so as to couple the lead to the electronic circuits within the implantable stimulation device via the feedthrough assembly. Needless to say, it is imperative that completely dependable electrical contact be made between the lead and the connector assembly. At the same time, the connector assembly must be capable of releasing the lead from the lead receptacle during a subsequent surgical procedure, and must also tightly seal against the entry of body fluids.

It is known in prior art connector assemblies to make electrical connection to one or more terminals on the lead by means of a variety of connector assemblies including a captive fastening screw/collet arrangement; a setscrew; and a spring or other compliant electrical contact. It is also known to use a prefabricated connector assembly to hold the electrical contacts together with a series of nonconductive spacers which are made from plastic. The resulting connector subassembly is attached to the pacemaker, or other implantable device, by fixturing it over the pacemaker and having epoxy molded around the subassembly. Alternatively, the connector subassembly may be inserted into a pre-molded connector top and bonded to the pacemaker.

In those prior art connector assemblies in which the lead is fixed within the lead receptacle using a setscrew, the setscrew is often threaded into a connector block within the connector assembly. When the screw is advanced, it comes into physical contact with the tip terminal of the lead. The resulting physical connection is often used as the electrical contact as well. However, this can present one or more problems. For example, the lead is sometimes damaged by the force produced when the setscrew is tightened. Such damage must be controlled, inasmuch as the life of the lead is often longer than that of the pacemaker. Additionally, setscrews in prior art connector assemblies have a history of stripping out of the threaded block. Particularly where relatively small setscrews are used, the threads, or the hex flats, may strip. To minimize or eliminate such problems, setscrews of a certain minimum physical size are necessary. The result is often a hump on the side of the connector assembly as the physical size of the pacemaker and its connector assembly are reduced.

A further problem of prior art setscrew type connector assemblies arises from the need to isolate the setscrew and the setscrew block from bodily fluids. One solution has been to use a silicone seal called a septum. The septum forms an insulation barrier between the setscrew and bodily fluids. However, the septum must permit a wrench to pass through it so that the screw can be tightened. Frequently, the septum is damaged by the wrench resulting in a loss of the insulation barrier.

U.S. Pat. No. 5,951,595 issued Sep. 14, 1999, and incorporated herein by reference in its entirety, discloses a connector assembly mounted on an implantable cardiac stimulation device having an actuator mechanism for fixing and tightly sealing electrical leads inserted into lead receptacles within the connector assembly without the use of setscrews. Fixing and sealing of the leads is accomplished by compressing resilient lead lock seals of O-ring shape, disposed in annular recesses, with lip portions of a plunger drawn toward a molded support by the actuator mechanism. In a first embodiment of the actuator mechanism of the '595 patent, rotation of a cam actuator transversely journaled within the support, using a torque wrench or similar tool, moves a cam slide attached to the plunger through a fixed displacement between lock and unlock positions as an offset camming portion of the actuator engages the surfaces of a slot within the cam slide. In a second embodiment of the actuator mechanism of the '595 patent, constant-force compression of the lead lock seals by the plunger is provided by using a torque wrench to rotate a screw actuator having one end coupled to the plunger and an opposite threaded end received within a screw block transversely disposed within the support. The screw actuator is oriented longitudinally, that is, its axis is parallel with the longitudinal axes of the lead receptacles, and includes an enlarged driver end projecting from the front end of the plunger in between the leads extending from the lead receptacles. In a third embodiment of the actuator mechanism of the '595 patent, the actuator comprises a rotatable toothed pinion engages a toothed slot within a slidable rack to provide incremental advancement of the rack, and thereby stepped displacement and applied force, with a resulting increased resolution. In a fourth embodiment of the mechanism of the '595 patent, compliance provided by either a spring formed within the cam slide, or a spring nut mounted thereon, prevents excessive force from being exerted on leads of larger diameter.

The connector assembly of the '595 patent overcomes the disadvantages of earlier connector assemblies employing lead fixation techniques using setscrews. In addition, unlike the second embodiment of the '595 patent utilizing a front actuated, longitudinally extending screw actuator, the first embodiment of the '595 patent employing a cam actuator transversely journaled within the support has the advantage of providing unobstructed access to the actuator from the side of the assembly thereby speeding the fixation of the leads in the lead receptacles as well as their removal. A side actuated connector assembly is thus preferred by implanting physicians over a front actuated connector assembly. It has been found, however, that cam actuators do not provide the high resolution displacement of the plunger or constant force compression of the lead lock seals provided by screw actuators.

Accordingly, it would be desirable to provide a side actuated connector assembly for securing or fixing and sealing an implantable stimulation device lead within a lead receptacle that at the same time provides high resolution plunger displacement together with constant force compression of the lead lock seals.

SUMMARY OF THE INVENTION

In accordance with one specific, exemplary embodiment of the invention, there is provided a connector assembly for an implantable stimulation device, the connector assembly comprising a support having opposed sides and a longitudinally extending chamber formed therein, and a connector bore assembly coupled to and extending from the chamber in the support, the connector bore assembly being adapted to make electrical contact with a lead insertable in the chamber formed in the support. The connector assembly further includes a plunger movably coupled to the support, the plunger having a chamber aligned with the chamber in the support, the chambers in the support and in the plunger combining with the connector bore assembly to define a lead-receiving receptacle. Disposed within the lead-receiving receptacle is a locking seal, the connector assembly further comprising an actuator for selectively moving the plunger relative to the support to compress the locking seal and thereby fix a lead inserted in the lead-receiving receptacle and form a seal around said lead. The actuator includes a longitudinally extending, rotatable threaded shaft threadedly connected to the plunger and a driver element carried by the support for rotating the threaded shaft. The driver element is accessible from one of the sides of the support allowing the driver element to be rotated by means of a torque limiting wrench, for example, thus facilitating insertion and removal of the lead without obstruction.

In accordance with another aspect of the present invention, the actuator for moving the plunger is movable between a first position in which the seal engages the lead to fix the lead in place and form a seal there around and a second position in which the seal is disengaged from the lead to permit removal of the lead from the lead-receiving receptacle. Further, the threaded shaft is rotatable about a longitudinally extending axis, the driver element has an axis of rotation, and a transmission is provided for converting rotation of the driver element about the rotational axis thereof to rotation of the threaded shaft about its axis. More specifically, the longitudinal axis of the threaded shaft and the rotational axis of the driver element may be perpendicular to each other, the transmission including a bevel gear on the driver element in mesh with a driven bevel gear on the threaded shaft.

In accordance with yet another specific feature of the invention, the plunger includes a longitudinally extending, internally threaded member in threaded engagement with the threaded shaft. The threaded member on the plunger preferably comprises a split retention clamp having a plurality of longitudinally extending fingers. Further in this regard, the threaded shaft includes an outer surface and a flange projecting outwardly from the outer surface. Each of the plurality of fingers on the retention clamp includes an inwardly projecting shoulder, the shoulders on the fingers being adapted to be engaged by the flange when the actuator is fully open, thereby arresting further movement of the plunger.

It will be seen that the present invention provides a side actuated connector assembly preferred by implanting physicians, while at the same time providing by way of a screw actuator, high resolution plunger displacement together with constant force compression of the lead locking seal.

In accordance with still further embodiments of the invention, the connector assembly of the present invention can be designed to accommodate only a single lead for providing stimulation to and sensing from the tissue of a single heart chamber, or two leads for dual-chamber stimulation and single or dual-chamber sensing, or three or four leads for multi-site or multi-chamber stimulation and sensing.

BRIEF DESCRIPTION OF THE DRAWINGS

Further objects, features and advantages of the invention will become evident from the detailed description below when read in conjunction with the accompanying drawings in which:

FIG. 11 is another perspective view of the bevel gear drive assembly or actuator of FIG. 10;

DETAILED DESCRIPTION OF THE PREFERRED EMBODIMENTS

Figure 1:
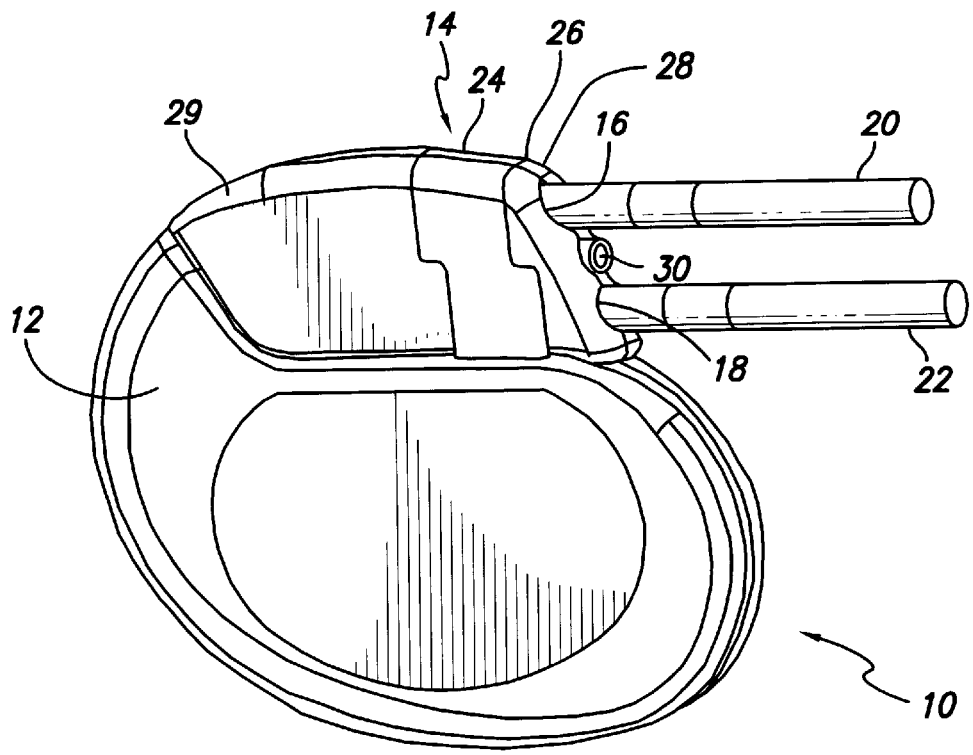
FIG. 1 is a perspective view of a cardiac pacemaker having a connector assembly in accordance with the prior art.

FIG. 1 shows a prior art cardiac pacemaker 10 of conventional design, including a housing or pacer can 12 enclosing the electronic components of the pacemaker and a connector assembly 14 along the top edge of the pacemaker. The connector assembly 14 includes a pair of receptacles 16 and 18 for receiving a pair of conventional bipolar leads 20 and 22 for dual chamber pacing and sensing in accordance with techniques well known in the art. The connector assembly 14 includes a molded support 24 having a front end 26 carrying a movable plunger 28. An epoxy casting 29 at the rear end of the support 24 encloses the electrical connections (not shown) extending rearwardly from the lead receptacles 16 and 18. The prior art pacemaker 10 incorporates a screw actuated lead fixation and sealing mechanism of the kind shown in FIGS. 10–18 of the '595 patent and described in the associated portions of the specification of that patent. As noted earlier, fixing and sealing of the leads 20 and 22 are accomplished by compressing resilient, O-ring like lead lock seals disposed in annular recesses in the molded support 24 by means of the plunger 28 which is drawn toward the molded support 24 by the screw actuator. The screw actuator includes an exposed head in the form of a hex driver 30 projecting from the front of the plunger 28.

As shown in FIG. 1, the hex driver 30 is positioned between the leads 20 and 22 when the leads are installed in the connector assembly 14. During implantation of the pacemaker, the implanting physician inserts the leads 20 and 22 into the receptacles 16 and 18 defined by the connector assembly 14. To fix and seal the leads within their respective receptacles, the physician must then actuate the plunger 28 of the connector assembly by inserting a torque wrench into the hex driver 30 and turning the wrench. However, the leads 20 and 22 often obstruct the physician's ability to freely rotate the torque wrench. Moreover, during explantation, when it is necessary to remove the leads from the connector assembly 14, fibrotic growth may have formed between the leads often obstructing the physician's ability to insert the torque wrench into the cavity of the hex driver 30. Accordingly, a scalpel may have to be used to remove the fibrotic tissue in the region of the hex driver in order to insert the torque wrench in the hex driver cavity. This procedure involves risk. For example, if the physician accidentally cuts one of the leads, replacement thereof is a significant procedure.

For this reason, implanting physicians prefer side actuated connector assemblies over front actuated assemblies. At the same time, however, the screw actuated connector assemblies of the prior art are advantageous in being able to provide high resolution plunger displacement together with constant force compression of the lead lock seals on leads having various diameters and material hardnesses.

Figure 2:
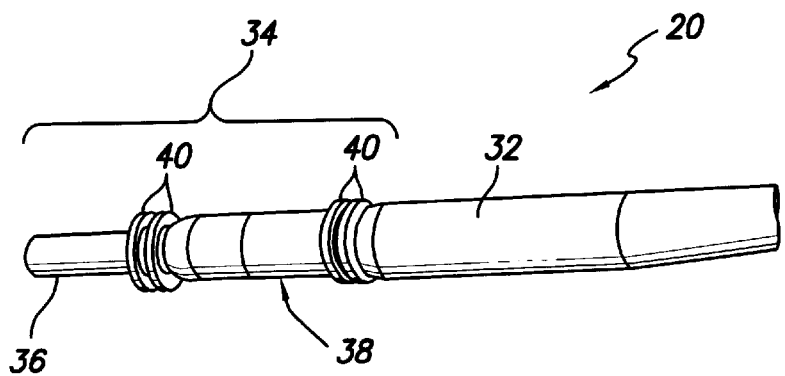
FIG. 2 is a perspective view of the proximal end portion of a conventional bipolar pacing lead.

FIG. 2 shows the details of a portion of the lead 20 which is taken as representative. The lead 20 is a conventional transvenous, bipolar coaxial pacing lead of sufficiently small diameter to facilitate implantation into small veins and to allow implantation of a plurality of leads into a single vessel for dual- or multi-chamber pacing. The particular bipolar lead of FIG. 2 is a common example of a cardiac pacemaker lead, and is useful in understanding the connector assemblies described hereafter. It should be understood, however, that other lead designs can be used in accordance with the invention. Depending upon the type of cardiac pacemaker, there may be one, two or more of the leads corresponding to single-chamber, dual-chamber or multi-chamber pacemakers. Also, while the lead of FIG. 2 is of the bipolar variety, there are unipolar leads which contain but a single electrode.

As is well known in the art, bipolar coaxial leads such as the lead 20 typically consist of an inner multifilar conductor coil which is surrounded by an inner insulation tube. This inner conductor coil connects to a tip electrode on the distal end of the lead. The assembly is then surrounded by a separate, outer multifilar conductor coil which is enclosed by an outer insulation 32. The outer conductor coil is connected to an anodal ring electrode along the distal end portion of the lead. The inner insulation is intended to electrically isolate the two conductor coils preventing any internal electrical short circuit, while the outer insulation 32 protects the entire lead from the intrusion of body fluids. These insulation materials are typically either silicone rubber or polyurethane. Recently, there have been introduced bipolar leads in which a multifilar cable is substituted for the outer conductor coil in order to reduce even further the overall diameter of the lead.

The bipolar lead 20 shown in FIG. 2 has a proximal or connector end portion 34 provided with a pair of spaced apart terminals including a tip terminal 36 and a ring terminal 38. The tip terminal 36 is electrically connected by means of the inner conductor coil to the tip electrode at the distal end of the lead, while the ring terminal 38 is electrically connected to the anodal ring electrode. The tip and ring terminals of the lead 20 may each be engaged by conductive springs or other resilient members within the connector assembly to make electrical contact with the connector end of the lead. Seal rings 40 are disposed along opposite ends of the ring terminal. For convenience of illustration, only a portion of the lead is shown in FIG. 2. With the proximal end of the lead 20 mounted within the lead receptacle 16 of a connector assembly 14, the terminals 36 and 38 are electrically coupled to the electronic circuits within the attached cardiac pacemaker, or other implantable tissue stimulation device.

Figure 3:
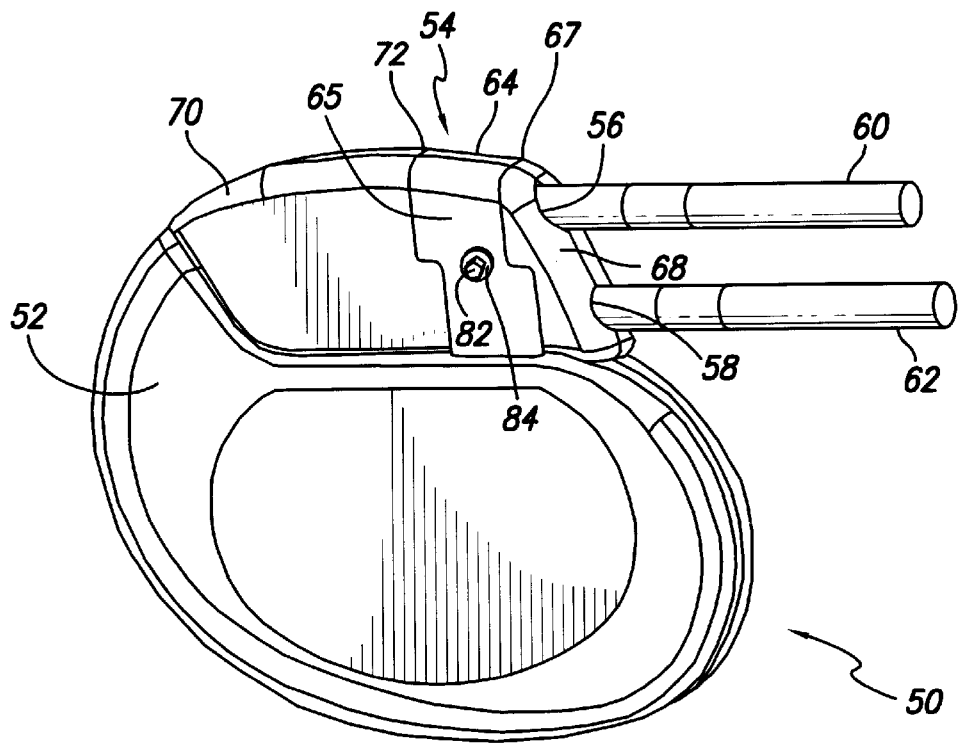
FIG. 3 is a perspective view of a cardiac pacemaker having mounted along the top thereof a connector assembly in accordance with one specific exemplary embodiment of the present invention.
Figure 4:
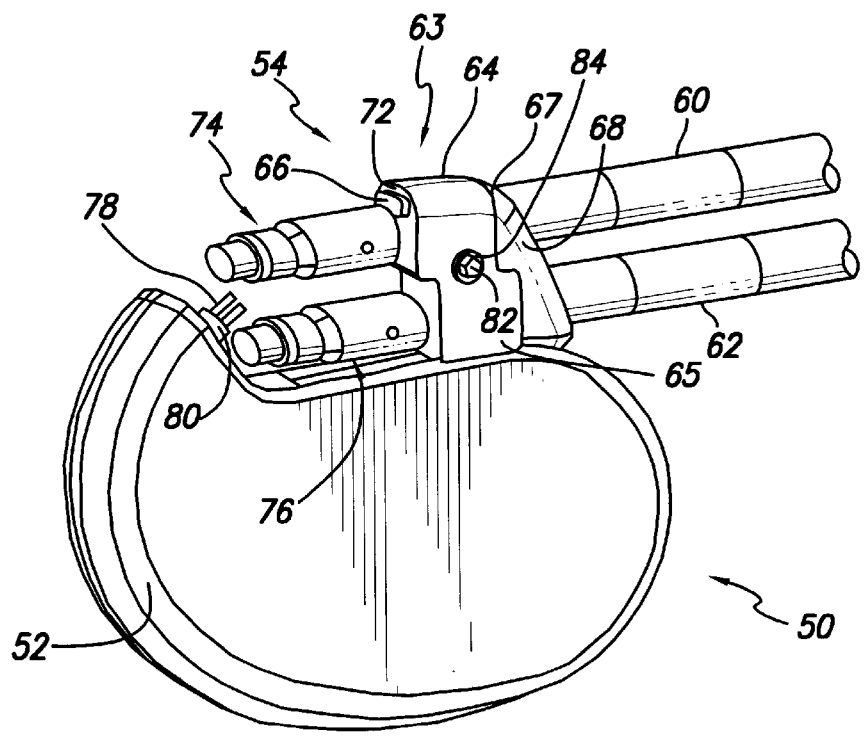
FIG. 4 is a perspective view of the cardiac pacemaker of FIG. 3 having removed therefrom the epoxy casting so as to expose rearwardly extending connector bore assemblies forming part of the connector assembly.
Figure 5:
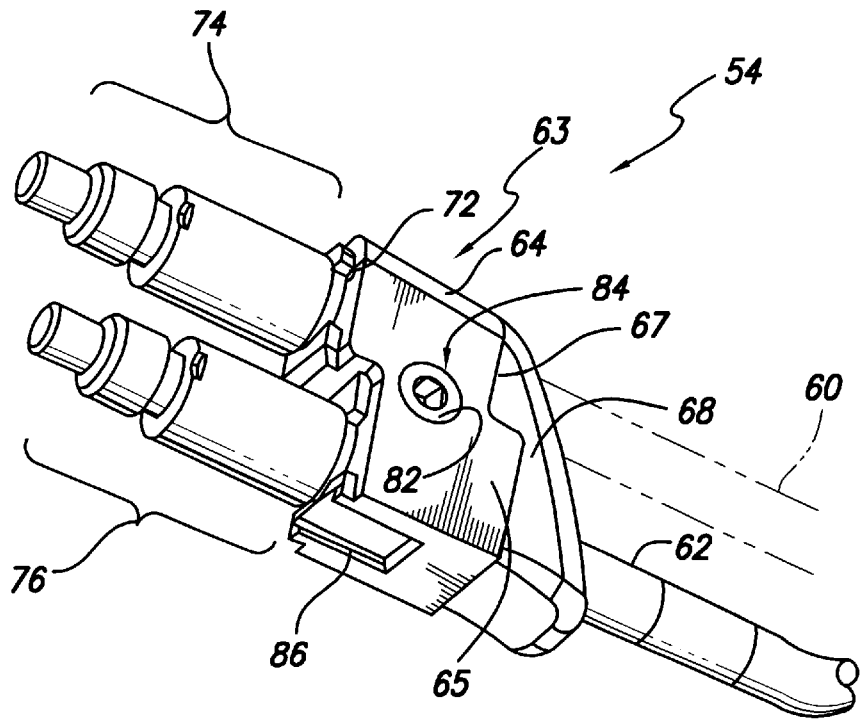
FIG. 5 is a perspective view of the connector assembly forming part of the pacemaker depicted in FIGS. 3 and 4.
Figure 6:
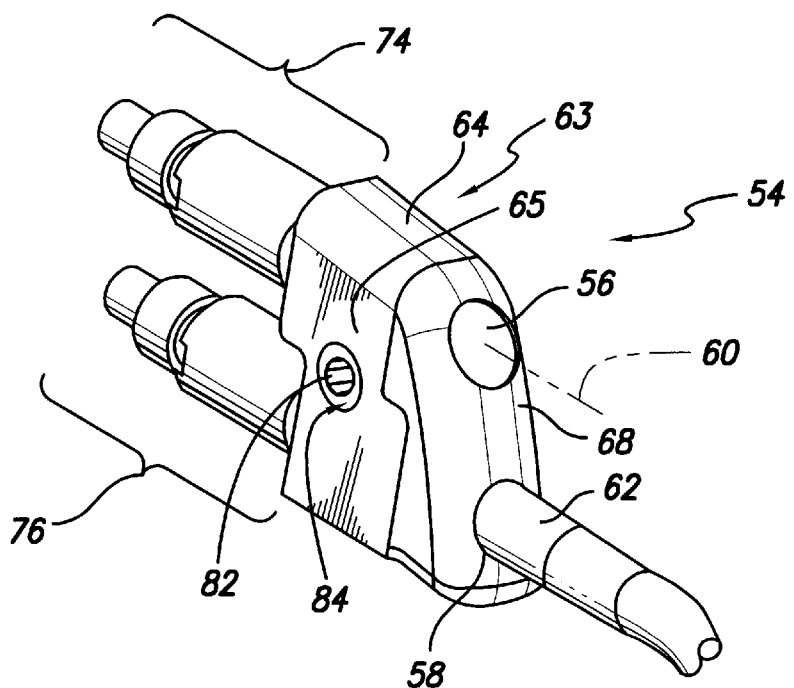
FIG. 6 is a different perspective view of the connector assembly of FIG. 5.

FIGS. 3 and 4 show a cardiac pacemaker 50 in accordance with one specific exemplary embodiment of the present invention. Again, the cardiac pacemaker 50 incorporating the invention is basically of conventional design, including a housing or pacer 52 can enclosing the electronic components of the pacemaker and a connector assembly 54 along the top edge of the pacemaker. Perspective views of the connector assembly 54 are shown in FIGS. 5 and 6. As before, the connector assembly 54 includes a pair of receptacles 56 and 58 for receiving conventional bipolar leads 60 and 62 for dual-chamber pacing and sensing in accordance with techniques well known in the art. The connector assembly 54 includes an actuator mechanism 63 comprising a molded support 64, a movable plunger 68 and a screw driven actuator described below. The support 64 has sides 65 and 66 and a front end 67 carrying the movable plunger 68. An epoxy casting 70 at the rear end 72 of the support 64 encloses the electrical connections extending rearwardly from the lead receptacles 56 and 58. As seen in FIG. 4 which shows the pacemaker 50 with the epoxy casting 70 removed, such electrical connections include a pair of connector bore assemblies 74 and 76 that are coupled to the pins 78 of a feedthrough assembly 80 by means of ribbon conductors (not shown). As is known, the pins 78 of the feedthrough assembly 80 are connected to the electronic components of the pacemaker hermetically sealed within the pacer can 52. As mentioned, the actuator mechanism 63 incorporates a screw driven lead fixation and sealing actuator. That actuator includes an exposed, side mounted actuator mechanism driver element or gear nut 82 journaled within an opening 84 formed in the side 65 of the molded support. Rotation of the screw actuator by means of the driver element or gear nut 82 moves the plunger 68 between opposite, first and second positions to selectively lock or unlock the leads 60 and 62 seated in the lead receptacles 56 and 58 within the connector assembly 54.

As shown in FIG. 5, the connector assembly 54 includes a dovetail mount 86 at the bottom of the molded support 64 to facilitate mounting of the connector assembly on the top of a cardiac pacemaker 50, in a manner well known in the art.

Figure 7:
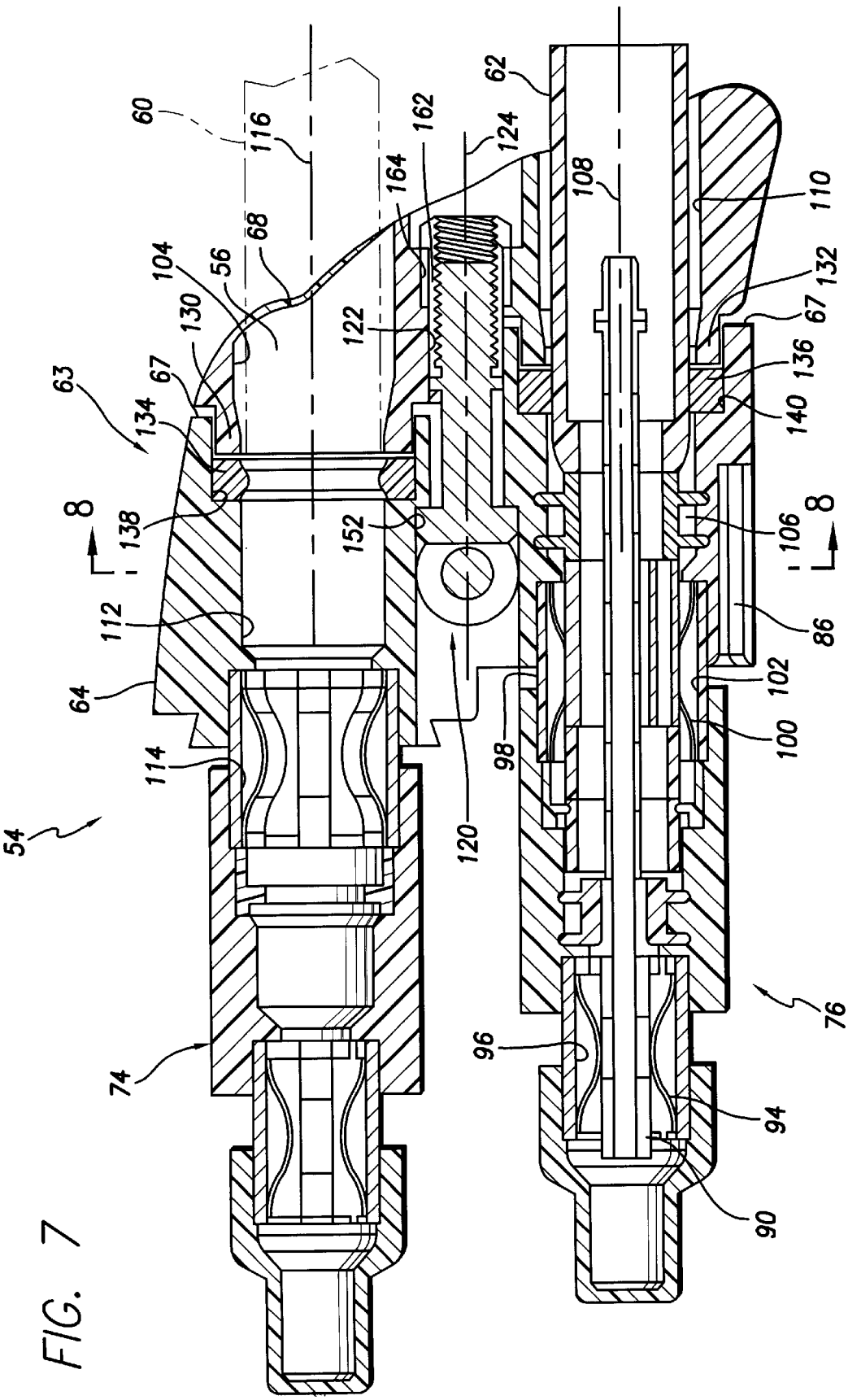
FIG. 7 is a side elevation view, in cross-section, of the connector assembly of FIGS. 3–6.
Figure 8:
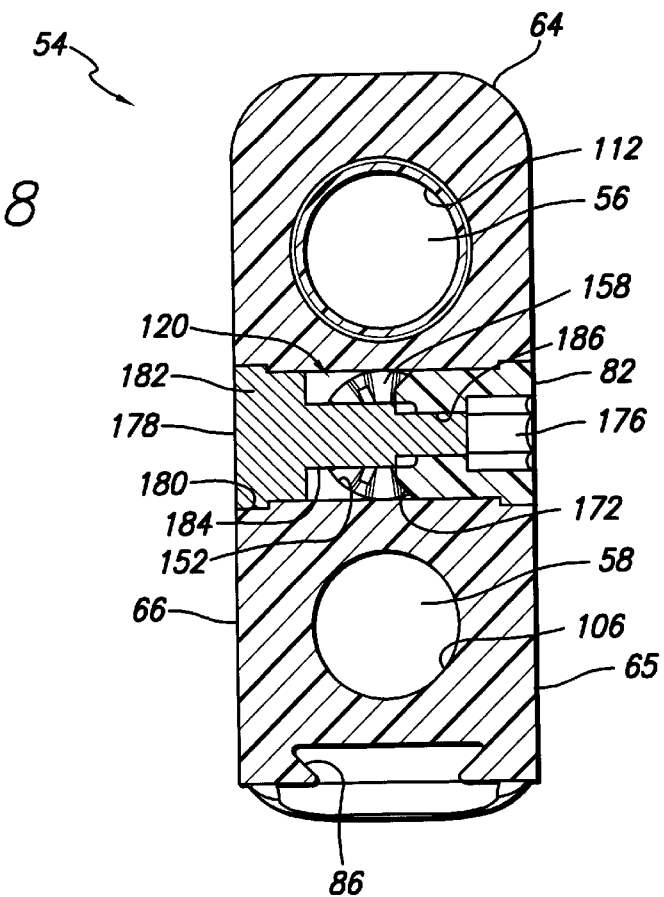
FIG. 8 is a cross-section view of a portion of the connector assembly as seen along line 8—8 in FIG. 7.
Figure 12:
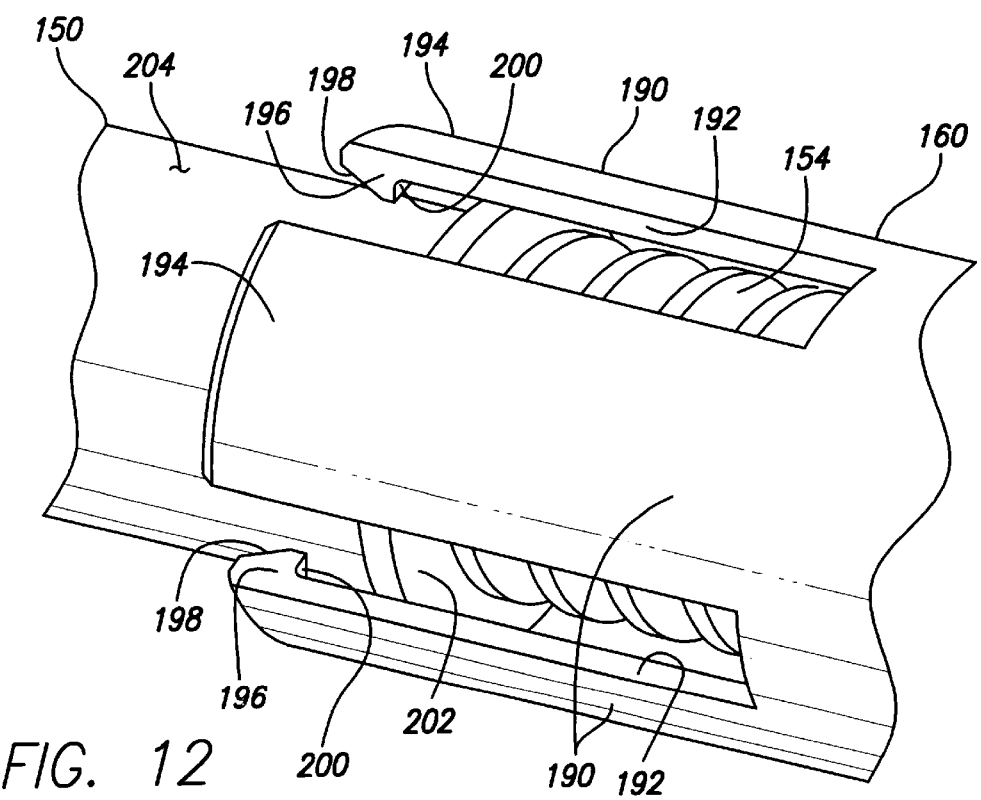
FIG. 12 is an enlarged perspective view of a portion of the bevel gear drive assembly of FIGS. 10 and 11.
Figure 9:
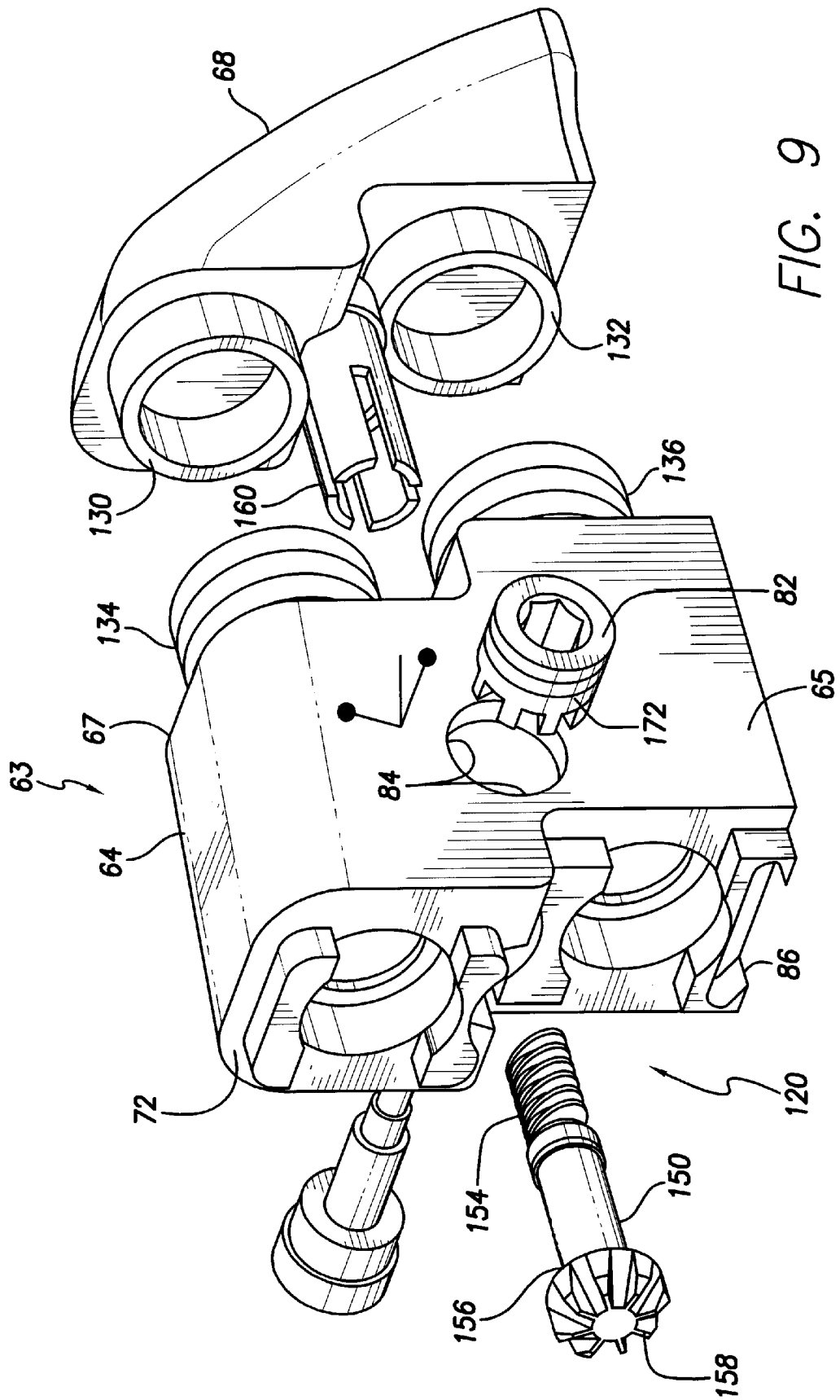
FIG. 9 is an exploded, perspective view of portions of the actuator mechanism forming part of the connector assembly of FIGS. 3–8.
Figure 10:
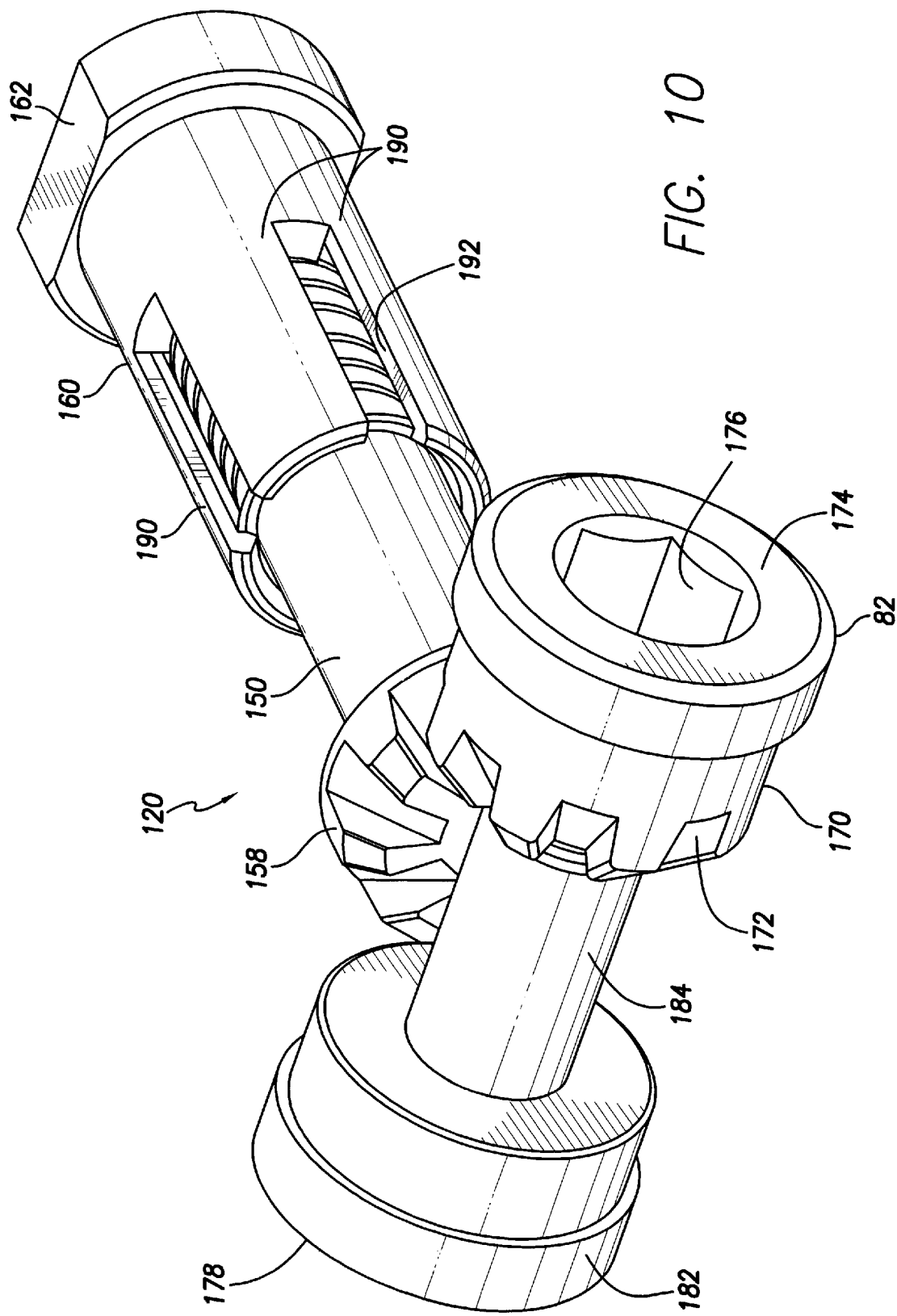
FIG. 10 is a perspective view of a bevel gear drive assembly or actuator forming part of the actuator mechanism of FIG. 9.

FIGS. 7 and 8 are cross-section views of the connector assembly 54. In FIG. 7, the lead 62 is shown seated within the lead receptacle 58. The lead 62 is a bipolar lead having a configuration similar to the lead 20 shown in FIG. 2. As such, the lead 62 has a tip terminal 90 at a proximal end 92 (i.e., proximal to the pacemaker), which is engaged by electrical contacts 94 within an elongated hollow interior 96 of the connector bore assembly 76. The proximal end 92 also includes a ring terminal 98 engaged by electrical contacts 100 within an elongated hollow interior 102. The lead receptacle 58 is comprised of a plunger chamber 104 within the plunger 68, a cylindrical support chamber 106 within the molded support 64, and the elongated hollow interior 102 of the connector bore assembly 76. The plunger chamber 104, the cylindrical support chamber 106 and the elongated hollow interior 102 have a common central axis 108 which defines the central axis of the lead receptacle 58. In similar fashion, the lead receptacle 56 is comprised of a plunger chamber 110 within the plunger 68, a cylindrical support chamber 112 within the molded support 64, and an elongated hollow interior 114 within the connector bore assembly 74. The plunger chamber 110, the cylindrical support chamber 112 and the elongated hollow interior 114 have a common central axis 116 which defines the central axis of the lead receptacle 56.

As previously noted, fixation and sealing of the leads, such as the lead 62 shown in FIG. 7, is accomplished using a screw actuator identified by the reference numeral 120 which forms part of the actuator mechanism 63. The actuator 120 is shown in cross-section in FIGS. 7 and 8 within a bore 122 bridging the support 64 and plunger 68. The bore 122 has a central, longitudinal axis 124 parallel with the axes 108 and 116 and midway between those axes. Rotation of the actuator 120 moves the plunger 68 toward or away from the molded support 64. Rotation of the screw actuator 120 in one direction causes upper and lower annular lip portions 130 and 132 extending from the plunger 68 to compress lead lock seals 134 and 136 which are seated within annular recesses 138 and 140, respectively, at the front end 67 of the molded support 64. The annular recesses 138 and 140 surround the entrances to the cylindrical support chambers 112 and 106, respectively, within the molded support 64. The lead lock seals 134 and 136 are ring-like in shape, and comprise O-rings in the present example. They are made of appropriate resilient, elastomeric material such as silicone. Compression of the lead lock seals 134 and 136 by the annular lip portions 130 and 132 of the plunger 64 presses the lead lock seals 134 and 136 against the leads inserted within the lead receptacles 56 and 58 so as to fix and seal the leads therein.

FIG. 7 shows the lead 62 installed within the lead receptacle 58; lead 60, shown in phantom, would be installed in the lead receptacle 56. Consequently, compression of the lead lock seal 136 by the annular lip portion 132 presses the lead lock seal 136 against the lead 62. This secures or fixes the lead 62 within the lead receptacle 58. It also seals the lead receptacle 58 to prevent entry of body fluids therein. Rotation of the screw actuator mechanism in the opposite direction moves the plunger 68 to the right as viewed in FIG. 7 to decompress or release the lead lock seals 134 and 136, so that the leads 60 and 62 installed within the lead receptacles 56 and 58 can be removed.

Because the support is molded of a material such as polysulfone, the connector bore assemblies, which are of essentially conventional configuration, can be press fitted into place within the molded support. When so assembled, the molded support and the included connector bore assemblies form a modular portion of the connector assembly, which may be mounted on a cardiac pacemaker using the dovetail mount. The plunger, which may also be made of polysulfone or other appropriate material, is movably joined to the molded support in a manner described hereafter.

FIGS. 9–12 show details of the actuator mechanism 63 and the screw actuator 120 forming part of the mechanism 63. The screw actuator 120 provides a constant retention force on leads having various diameters and material hardnesses. The screw actuator 120 of the invention also provides higher displacement resolution than, for example, cam-operated actuators.

The screw actuator 120 includes a gear shaft 150 journaled in a central, longitudinally extending bore 152 (see FIG. 7) formed in the molded support 64. In the embodiment under consideration, the bore 152 has a central, longitudinally extending axis coincident with the axis 124. The axis 124 is disposed parallel with and equidistant from the longitudinal axes 108 and 116 of the lead receptacles 56 and 58 and connector bore assemblies 74 and 76 so that the retention forces applied to the two leads 60 and 62 will be substantially equal or balanced when the mechanism 120 is fully actuated. The gear shaft 150 has a threaded front end portion 154 and a rear extremity 156, opposite the front end portion, carrying a driven bevel gear 158. The threaded front end portion 154 of the gear shaft is received by a threaded retention clamp 160 having an enlarged head 162 received by a corresponding cavity 164 in the plunger 68 (FIG. 7). The retention clamp 160 may be insert molded to the plunger 68 or, alternatively, comolded therewith. Thus, rotation of the gear shaft 150 in one direction draws the plunger 68 toward the support 64 while rotation of the gear shaft 150 in the opposite direction moves the plunger 68 away from the support 64.

The molded support 64 includes in the side wall 65 thereof the transverse opening or bore 84 within which the gear nut 82 is journaled. The gear nut 82 has an inner end 170 carrying a drive bevel gear 172 in mesh with the driven bevel gear 158 on the gear shaft 150, and an outer end 174 accessible by the implanting physician, including a cavity 176 having a hexagonal shape, by way of example, for receiving a torque limiting wrench. The gear nut 82 is constrained transversely by means of a retainer 178 inserted in a transverse bore 180 (FIG. 8) in the side wall 66 of the support 64 coaxial with the gear nut bore 84. The retainer 178 includes an outer, enlarged head 182 and an inner shaft 184 received by a central opening 186 in the gear nut 82, and welded to the gear nut.

The retention clamp 160 that threadedly receives the gear shaft 150 comprises a split structure including a plurality, for example, four fingers 190 defined by longitudinal slots 192 extending rearwardly and of sufficient length to impart some flexibility to the fingers 190 so that the fingers may be forced apart to a limited extent. The rear extremity 194 of each of the fingers is provided with an inwardly extending shoulder 196 having a tapered rear surface 198 and a front, radially oriented surface 200 adapted to engage a flange 202 projecting from the outer surface 204 of the gear shaft 150 adjacent the rear extremity of the threaded portion 154 thereof. It will thus be seen that during initial assembly of the gear shaft 150 and retention clamp 160, the gear shaft is screwed into the retention clamp until the shoulders 196 at the rear extremities of the flexible fingers 190 ride up and over the flange 202 until the fingers snap back to their unflexed position shown in FIGS. 10–12.

To actuate the mechanism, using a torque limiting wrench the driver element or gear nut 82 is rotated clockwise to open the connector assembly 54 to decompress and release the leads 60 and 62 and counterclockwise to close the connector assembly to fix and seal the leads within the lead receptacles 56 and 58. When fully open, the actuator mechanism 120 will stop due to the radial surfaces 200 on the finger shoulders 196 coming into contact with the flange 202 on the outer surface 204 of the threaded shaft 150. Besides arresting further movement of plunger 68, the engaged shoulders 196 and flange 202 prevent the plunger 68 from coming loose from the assembly. When fully closed, the plunger 68 will have moved toward the support 64 until the limiting force of the torque wrench is reached or the seals cannot be compressed any further on the leads.

The design of the screw operated actuator mechanism 63 of the present invention provides for high resolution plunger displacement together with the application of a predetermined amount of force to the lead lock seals, since there is variability in the displacement of the plunger. By using a torque wrench, for example, to rotate the driver element 82, the annular lip portions 130 and 132 of the plunger 68 compress the lead lock seals 134 and 136 a predetermined amount proportional to the torque limit preset in the torque wrench, thereby controlling the amount of force applied to the lead lock seals. Accordingly, for leads of different sizes or configurations, a predetermined amount of force can still be exerted against the leads seated within the lead receptacles. Further, the present invention provides for unobstructed access to the actuator from the side of the assembly.

Figure 13:
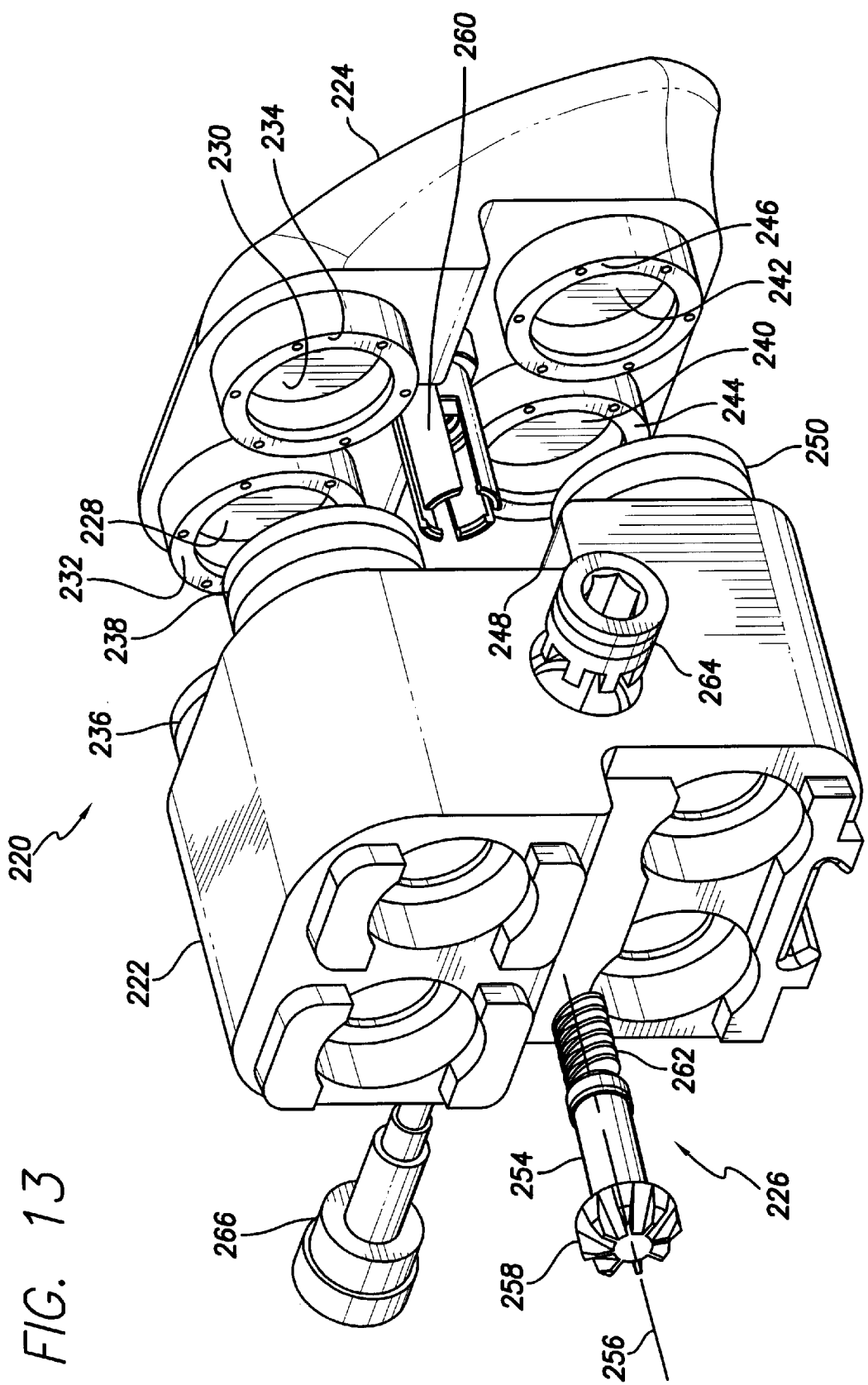
FIG. 13 is an exploded, perspective view of portions of an actuator mechanism forming part of a four-lead connector assembly in accordance with another example of the present invention.

FIG. 13 is a perspective, exploded view of a lead seal and retention actuator mechanism 220 for use in a connector assembly in accordance with another exemplary embodiment of the invention. A connector assembly incorporating the mechanism 220 is designed for use with a stimulation device in electrical communication with a patent's heart by way of four implantable, typically bipolar leads suitable for delivering multi-site or multi-chamber stimulation or pacing therapy as well as sensing in accordance with techniques well known in the art. Stimulation devices employing four leads are sometimes referred to as bi-ventricular, bi-atrial devices, or "4×4" devices, because all four chambers of the heart may be stimulated and sensed.

The actuator mechanism 220 is simply an extended version of the dual-chamber embodiment already described and, like the dual-chamber embodiment, basically comprises a molded support 222, a plunger 224 movable relative to the support 222, and a screw actuator 226 for moving the plunger 224 between opposite positions to selectively lock or unlock the leads. In this connection, the plunger 224 includes a pair of upper, transversely spaced apart lead receptacles 228 and 230 having associated therewith annular lip portions 232 and 234, respectively, for cooperating, in turn, with a corresponding pair of lead lock seals 236 and 238. The plunger 224 further includes a pair of lower, transversely spaced apart lead receptacles 240 and 242 having associated therewith annular lip portions 244 and 246, respectively, which are adapted to cooperate, in turn, with a corresponding pair of lead lock seals 248 and 250. Each of the four lead receptacles 228,230, 240 and 242 and related lock seal elements are adapted to cooperate with an inserted lead as already described in connection with the dual-chamber embodiment. The central, longitudinal axes of the four lead receptacles 228, 230, 240 and 242 are arranged symmetrically about the screw actuator 226 which comprises a threaded gear shaft 254 journaled for rotation in the support 222 about a central longitudinal axis 256. As in the dual-chamber embodiment, the screw actuator 226 further includes a driven bevel gear 258 mounted on the rear end of the gear shaft 254; a split, tubular retention clamp 260 mounted on the plunger 224 for receiving the threaded forward end 262 of the gear shaft 254; a hex bevel gear driver or gear nut 264 accessible from a side of the support 222; and a retainer 266 for transversely constraining the gear nut 264.

The actuator mechanism 220 operates in similar fashion to that of the dual-chamber embodiment, and provides similar benefits: side actuation with high resolution plunger displacement combined with balanced, constant force compression of all four lead lock seals 236, 238, 248 and 250.

Figure 14:
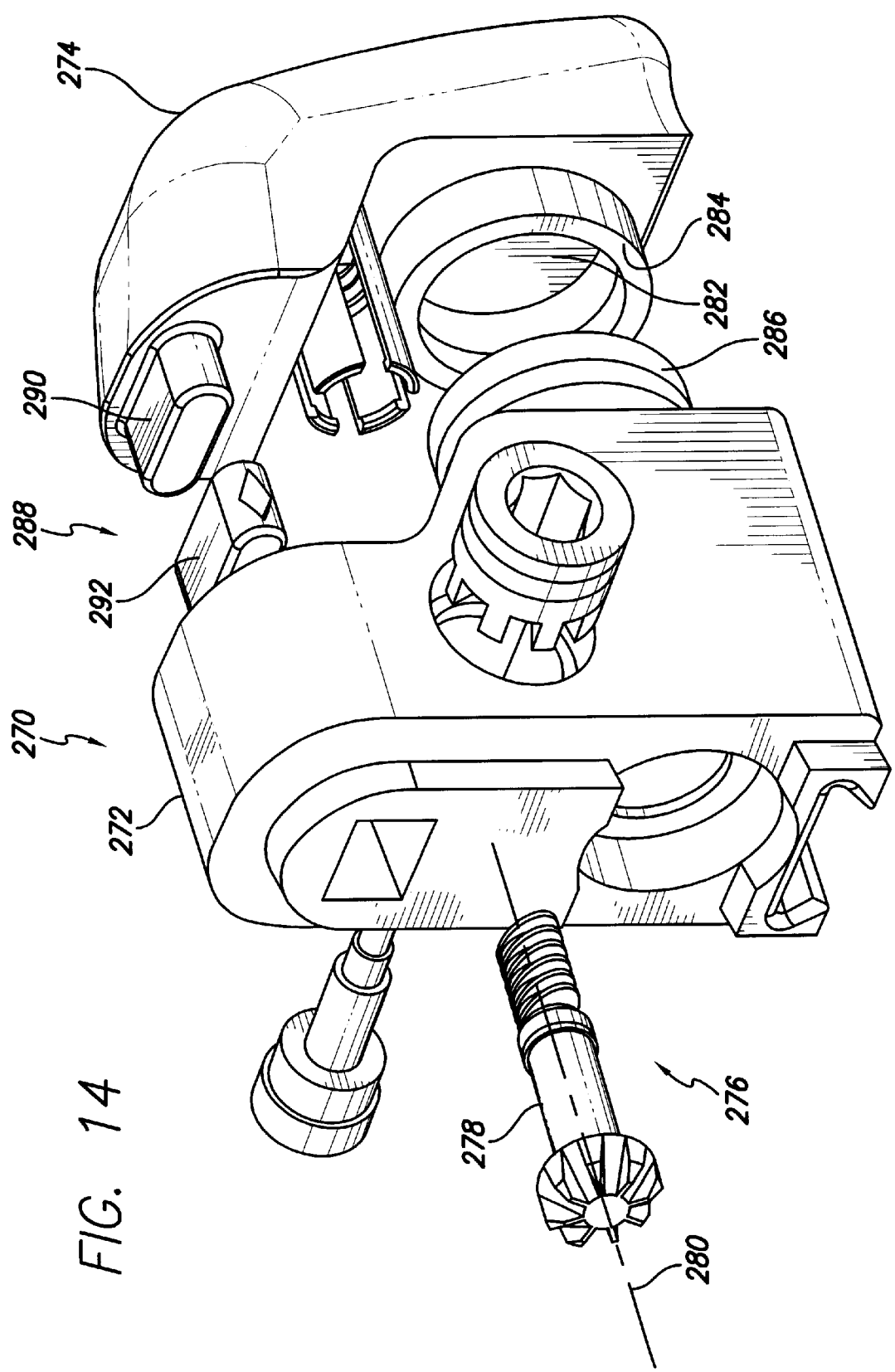
FIG. 14 is an exploded, perspective view of portions of an actuator mechanism forming part of a single lead connector assembly in accordance with yet another example of the present invention.

Turning now to FIG. 14, there is shown an exploded perspective view of a lead seal and actuator mechanism 270 for use in a connector assembly in accordance with yet another exemplary embodiment of the invention. A connector assembly incorporating the mechanism 270 is adapted to be used with a single lead stimulation device in electrical communication with a single chamber of a patient's heart. As before, the actuator mechanism 270 basically comprises a molded support 272, a plunger 274 movable longitudinally relative to the support 272, and a screw actuator 276 for moving the plunger 274 relative to the support 272 between opposite positions to selectively lock or unlock the single lead. The screw actuator 276 is identical to those previously described and, as before, includes a threaded gear shaft 278 journaled for rotation in the support 272 about a longitudinal axis 280. The plunger 274 includes a single, longitudinally extending lead receptacle 282 below the axis 280 and having associated therewith an annular lip portion 284 for cooperating, in turn, with a corresponding lead lock seal 286. Disposed above the axis 280 is a dummy port 288 including a plug 290 mounted on and projecting rearwardly from the plunger 274, and a resilient element 292, in longitudinal alignment with the plug 290, seated within a recess formed in the support 272.

In operation of the mechanism 270, rotation of the screw actuator 276 in the lead locking direction moves the plunger 274 toward the support 272 to compress the lock seal 286, in the manner already described. At the same time, the plug 290 engages and compresses the resilient element 292. By selecting a resilient element 292 having an appropriate spring constant, the forces exerted by the plunger when the screw actuator 276 is moved toward the lead lock position can be balanced about the axis 280. It will be evident to skilled artisans that the positions of the dummy port 288 and the lead receptacle 282 can be reversed.

While the present invention has been described with reference to particular illustrative embodiments, the invention is not intended to be restricted to those embodiments but only by the appended claims. It will be appreciated that those skilled in the art can change or modify the described embodiments, or substitute equivalents for the various elements described and shown, without departing from the scope and spirit of the invention.

What is claimed is:

1. A connector assembly for an implantable stimulation device, the connector assembly comprising:

a support having opposed sides and a longitudinally extending chamber formed therein;

a connector bore assembly coupled to and extending from the chamber in the support, the connector bore assembly being adapted to make electrical contact with a lead insertable in the chamber formed in the support;

a plunger movably coupled to the support, the plunger having a chamber aligned with the chamber in the support, the chambers in the support and in the plunger combining with the connector bore assembly to define a lead-receiving receptacle;

a locking seal disposed within the lead-receiving receptacle; and an actuator carried by the connector assembly for selectively moving the plunger relative to the support to compress the locking seal and thereby fix a lead inserted in the lead-receiving receptacle and form a seal around said lead, the actuator comprising a longitudinally extending, rotatable threaded shaft threadedly connected to the plunger and a driver element carried by the support for rotating the threaded shaft, the driver element being accessible from one of the sides of the support.

2. The connector assembly, as defined in claim 1, wherein:

the actuator for moving the plunger is movable between a first position in which the seal engages the lead to fix the lead in place and form a seal there around and a second position in which the seal is disengaged from the lead to permit removal of the lead from the lead-receiving receptacle.

3. The connector assembly, as defined in claim 1, in which:

the threaded shaft is rotatable about a longitudinally extending axis;

the driver element has an axis of rotation;

and in which the assembly further includes:

a transmission for converting rotation of the driver element about the rotational axis thereof to rotation of the threaded shaft about its axis.

4. The connector assembly, as defined in claim 3, in which:

the longitudinal axis of the threaded shaft and the rotational axis of the driver element are perpendicular to each other; and the transmission includes a bevel gear on the driver element in mesh with a driven bevel gear on the threaded shaft.

5. The connector assembly, as defined in claim 1, in which:

the plunger includes a longitudinally extending, internally threaded member in threaded engagement with the threaded shaft.

6. The connector assembly, as defined in claim 5, in which:

the threaded member on the plunger comprises a split retention clamp having a plurality of longitudinally extending fingers.

7. The connector assembly, as defined in claim 6, in which:

the plunger is movable by the actuator toward and away from the support;

the threaded shaft includes an outer surface and a flange projecting outwardly from said outer surface; and each of the plurality of fingers on the retention clamp includes an inwardly projecting shoulder, the shoulders on said fingers being adapted to be engaged by said flange at an extremity of the motion of the plunger away from the support.

8. In an implantable device for stimulating selected body tissue, the device including a sealed housing enclosing pulse generating electronic circuits, a connector assembly mounted on the housing for receiving a first electrical lead and a second electrical lead and for electrically coupling the first and second leads to the electronic circuits within the sealed housing, the connector assembly comprising:

a support having parallel, opposed sides, the support defining a first, longitudinally extending lead-receiving chamber and a second longitudinally extending lead-receiving chamber, each of said first and second chambers having a central, longitudinally extending axis, said axes being parallel with each other, said first and second chambers being adapted to receive the first lead and the second lead, respectively;

a locking seal, made of compressible material and disposed within each of the first and the second chambers, for providing a seal around each of the leads;

a plunger for compressing the locking seals around the first and second leads, thereby forming a first fluid-tight seal and a second fluid-tight seal, respectively; and an actuator carried by the connector assembly for selectively moving the plunger relative to the support to selectively lock and unlock the first and second leads in place to thereby fix the leads inserted in the lead-receiving chambers and form seals around said leads, the actuator comprising a longitudinally extending, rotatable threaded shaft threadedly connected to the plunger, the threaded shaft having a central, longitudinally extending axis parallel with, and disposed substantially midway between, the chamber axes, the actuator further including a rotatable driver element carried by the support, the driver element being coupled to the threaded shaft for rotating the threaded shaft to thereby move the plunger, the driver element being accessible from one of the sides of the support.

9. The connector assembly, as defined in claim 8, wherein:

the actuator for moving the plunger is movable between a first position in which each seal engages the lead associated with that seal to fix the lead in place and form a seal there around, and a second position in which each seal is disengaged from the lead associated with that seal to permit removal of the lead from connector assembly.

10. The connector assembly, as defined in claim 8, in which:

the driver element has an axis of rotation;

and in which the assembly further includes:

a transmission for converting rotation of the driver element about the rotational axis thereof to rotation of the threaded shaft about its axis.

11. The connector assembly, as defined in claim 10, in which:
   the longitudinal axis of the threaded shaft and the rotational axis of the driver element are perpendicular to each other; and
   the transmission includes a bevel gear on the driver element in mesh with a driven bevel gear on the threaded shaft.

12. The connector assembly, as defined in claim 8, in which:
   the plunger includes a longitudinally extending, internally threaded member in threaded engagement with the threaded shaft.

13. The connector assembly, as defined in claim 12, in which:
   the threaded member on the plunger comprises a split retention clamp having a plurality of longitudinally extending fingers.

14. The connector assembly, as defined in claim 13, in which:
   the plunger is movable by the actuator toward and away from the support;
   the threaded shaft includes an outer surface and a flange projecting outwardly from said outer surface; and
   each of the plurality of fingers on the retention clamp includes an inwardly projecting shoulder, the shoulders on said fingers being adapted to be engaged by said flange at an extremity of the motion of the plunger away from the support.

15. In an implantable device for stimulating selected body tissue, the device including a sealed housing enclosing pulse generating electronic circuits, a connector assembly mounted on the housing for receiving multiple electrical leads and for electrically coupling the multiple leads to the electronic circuits within the sealed housing, the connector assembly comprising:
   a support having parallel, opposed sides, the support defining multiple, longitudinally extending lead-receiving chambers, each of said multiple chambers having a central, longitudinally extending axis, said axes being parallel with each other, each of said multiple chambers being adapted to receive an electrical lead;
   a locking seal, made of compressible material and disposed within each of the multiple chambers, for providing a seal around each of the leads;
   a plunger for compressing the locking seals around the leads, thereby forming a fluid-tight seal around each lead; and
   an actuator carried by the connector assembly for selectively moving the plunger relative to the support to selectively lock and unlock the multiple leads in place to thereby fix the electrical leads inserted in the lead-receiving chambers and form seals around said leads, the actuator comprising a longitudinally extending, rotatable threaded shaft threadedly connected to the plunger, the threaded shaft having a central, longitudinally extending axis parallel with the chamber axes, the chamber axes being symmetrically disposed about the axis of the threaded shaft, the actuator further including a rotatable driver element carried by the support, the driver element being coupled to the threaded shaft for rotating the threaded shaft and thereby moving the plunger, the driver element being accessible from one of the sides of the support.

16. The connector assembly, as defined in claim 15, wherein:
   the actuator for moving the plunger is movable between a first position in which each seal engages the lead associated with that seal to fix the lead in place and form a seal there around, and a second position in which each seal is disengaged from the lead associated with that seal to permit removal of the lead from connector assembly.

17. The connector assembly, as defined in claim 15, in which:
   the driver element has an axis of rotation;
   and in which the assembly further includes:
      a transmission for converting rotation of the driver element about the rotational axis thereof to rotation of the threaded shaft about its axis.

18. The connector assembly, as defined in claim 17, in which:
   the longitudinal axis of the threaded shaft and the rotational axis of the driver element are perpendicular to each other; and
   the transmission includes a bevel gear on the driver element in mesh with a driven bevel gear on the threaded shaft.

19. The connector assembly, as defined in claim 15 in which:
   the plunger includes a longitudinally extending, internally threaded member in threaded engagement with the threaded shaft.

20. The connector assembly, as defined in claim 19, in which:
   the threaded member on the plunger comprises a split retention clamp having a plurality of longitudinally extending fingers.

21. The connector assembly, as defined in claim 20, in which:
   the plunger is movable by the actuator toward and away from the support;
   the threaded shaft includes an outer surface and a flange projecting outwardly from said outer surface; and
   each of the plurality of fingers on the retention clamp includes an inwardly projecting shoulder, the shoulders on said fingers being adapted to be engaged by said flange at an extremity of the motion of the plunger away from the support.

* * * * *